US012090187B1

(12) United States Patent
Lee et al.

(10) Patent No.: US 12,090,187 B1
(45) Date of Patent: Sep. 17, 2024

(54) METHOD FOR PREVENTING OR TREATING DISEASES RELATED TO VASCULAR ENDOTHELIAL CELL ACTIVITY REGULATION, COMPRISING A STEP OF ADMINISTERING JAVA PEPPER EXTRACT

(71) Applicant: NewTree Co., Ltd., Seoul (KR)

(72) Inventors: Jinhee Lee, Seoul (KR); Yuri Kwon, Yongin-si (KR)

(73) Assignee: NEWTREE CO., LTD., Seoul (KR)

( * ) Notice: Subject to any disclaimer, the term of this patent is extended or adjusted under 35 U.S.C. 154(b) by 0 days.

(21) Appl. No.: 18/204,345

(22) Filed: May 31, 2023

(51) Int. Cl.
| | |
|---|---|
| A61K 36/00 | (2006.01) |
| A61K 31/4525 | (2006.01) |
| A61K 36/67 | (2006.01) |
| A61K 47/36 | (2006.01) |
| A61P 9/00 | (2006.01) |

(52) U.S. Cl.
CPC .......... *A61K 36/67* (2013.01); *A61K 31/4525* (2013.01); *A61K 47/36* (2013.01); *A61P 9/00* (2018.01); *A61K 2236/331* (2013.01); *A61K 2236/333* (2013.01)

(58) Field of Classification Search
CPC ..................................................... A61K 36/67
See application file for complete search history.

(56) References Cited

FOREIGN PATENT DOCUMENTS

| CN | 107715062 A | * | 2/2018 |
| EP | 2647385 | | 10/2013 |

OTHER PUBLICATIONS

Sireeratawong et al, Anti-Inflammatory, Analgesic, and Antipyretic Activities of the Ethanol Extract of Piper interruptum Opiz. and Piper chaba Linn. ISRN pharmacology, (2012) vol. 2012, pp. 480265 (Year: 2012).*
Sharma et al, Piper officinarum: a potent antiatherosclerotic and hypolipidaemic agent. Indian Journal of Pharmaceutical Sciences (1998), vol. 60, No. 6, pp. 391-393 (Year: 1998).*
Ishii et al, Piper retrofractum extract and its component piperine promote lymphangiogenesis via an AKT- and ERK-dependent mechanism. Journal of Food Biochemistry (2022), vol. 46, No. 9 (Year: 2022).*
Neamsuvan, Medicinal plants used for hypertension treatment by folk healers in Songkhla province, Thailand. Journal of ethnopharmacology, (Mar. 25, 2018) vol. 214, pp. 58-70 (Year: 2018).*
Kim, Kyung Jin, et al. "Piperidine alkaloids from Piper retrofractum Vahl. protect against high-fat diet-induced obesity by regulating lipid metabolism and activating AMP-activated protein kinase." Biochemical and biophysical research communications 411.1 (Jul. 22, 2011): 219-225.
Dinanti, Bela Riski. "Long pepper (Piper retrofractum Vahl) to overcome erectile dysfunction." Majority: Medical Journal of Lampung University 3.7 (Dec. 2014). pp. 1-6.
Carvalho et al., "Use of ultrasound imaging software to differentiate venous and lymphatic edema in lower limbs", J. Vasc. Bras., 2020, 19:e20190139, https://doi.org/10.1590/1677-5449.190139, ISSN 1677-7301 (Online).
Pabla et al., "Effects of NO Modulation on Cardiac Arrhythmias in the Rat Isolated Heart", Cirbulation Research, 1995, 77(5): 984-992.
Paz et al., "Arterial versus venous endothelial cells", Cell Tissue Res., 2009, 335:5-16.
Suehiro et al., "Distribution of Extracellular Fluid in Legs with Venous Edema and Lymphedema", Lymphatic Research and Biology, 2016, vol. 00, No. 00, 6 pages.
Sunnarborg, "A Comparison Between Edema and Lymphedema", 1999, An Independent Study Submitted to the Graduate Faculty of the Department of Physical Therapy, School of Medicine, University of North Dakota, in partial fulfillment of the requirements for the degree of Master of Physical Therapy, 49 pages.
Troncoso et al., "VCAM-1 as a predictor biomarker in cardiovascular disease", BBA—Molecular Basis of Disease, 2021, 1867, 166170, 13 pages.
Wang et al., "Effect of TLR4/MyD88/NF-kB axis in paraventricular nucleus on ventricular arrhythmias induced by sympathetic hyperexcitation in post-myocardial infarction rats", J Cell Mol Med., 2021, 26: 2959-2971.

* cited by examiner

*Primary Examiner* — Qiuwen Mi
(74) *Attorney, Agent, or Firm* — James S. Keddie; Bozicevic, Field & Francis LLP

(57) ABSTRACT

The present application relates to use for anti-inflammation, and/or for prevention, improvement, and/or treatment of diseases related to vascular dysfunction of Java pepper extract, and provides a composition with an excellent anti-inflammatory effect and/or an excellent effect of prevention, improvement, and/or treatment of diseases related to vascular dysfunction, which is excellent in biosafety, by comprising Java pepper extract.

7 Claims, 8 Drawing Sheets

1. Roseoside; 2. Isovitexin-2''-O-glucoside; 3. Vitexin rhamnoside; 4. Rutin; 5. Piperchabaoside B; 6. Piperlongumine; 7. Piperyline; 8. Piperanine; 9. Piperine; 10. Pellitorine; 11. Pipernonaline; 12. Oleamide; 13. N-Isobutyl-2,4,12-octadecatrienamide

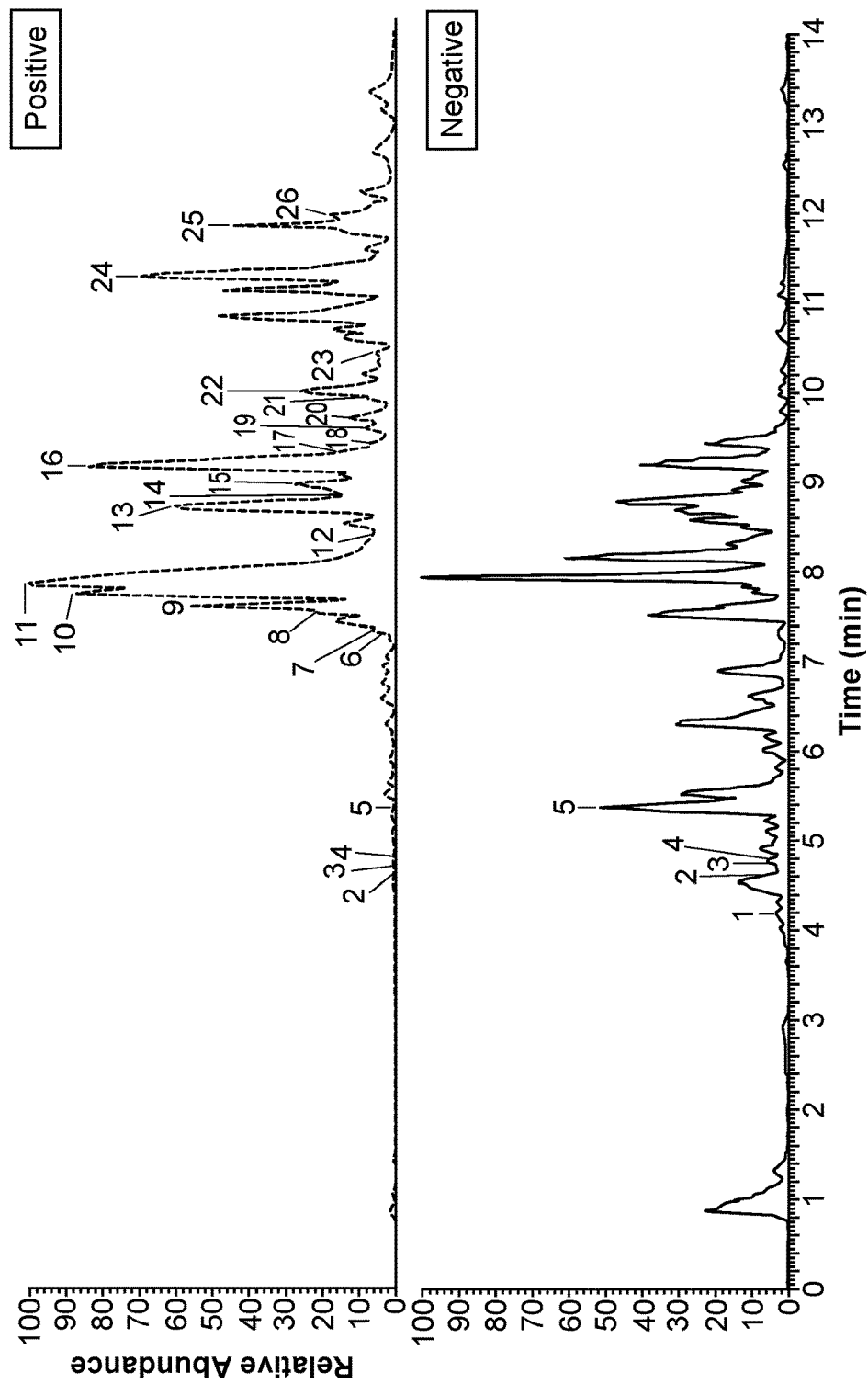

1. Roseoside; 2. Isovitexin-2''-O-glucoside; 3. Vitexin rhamnoside; 4. Rutin; 5. Piperchabaoside B; 6. Piperlongumine; 7. Piperyline; 8. Dihydropiperlonguminine; 9. Piperlonguminine; 10. Piperanine; 11. Piperine; 12. Piperdardine; 13. Pellitorine; 14. Pipercallosine; 15. Dehydropipernonaline; 16. Pipernonaline; 17. Retrofractamide B (Pipercide); 18. Piperolein B; 19. N-Isobutyl- 2,4-dodecadienamide; 20. Piperundecalidine; 21. Piperchabamide B; 22. Guineensine; 23. Piperchabamide C; 24. N-Isobutyl-2,4,12-octadecatrienamide; 25. 1-(2,4,12- Octadecatrienoyl)piperidine; 26. N-Isobutyl-2,4,14-eicosatrienamide

FIG. 2b

[FIG. 3]
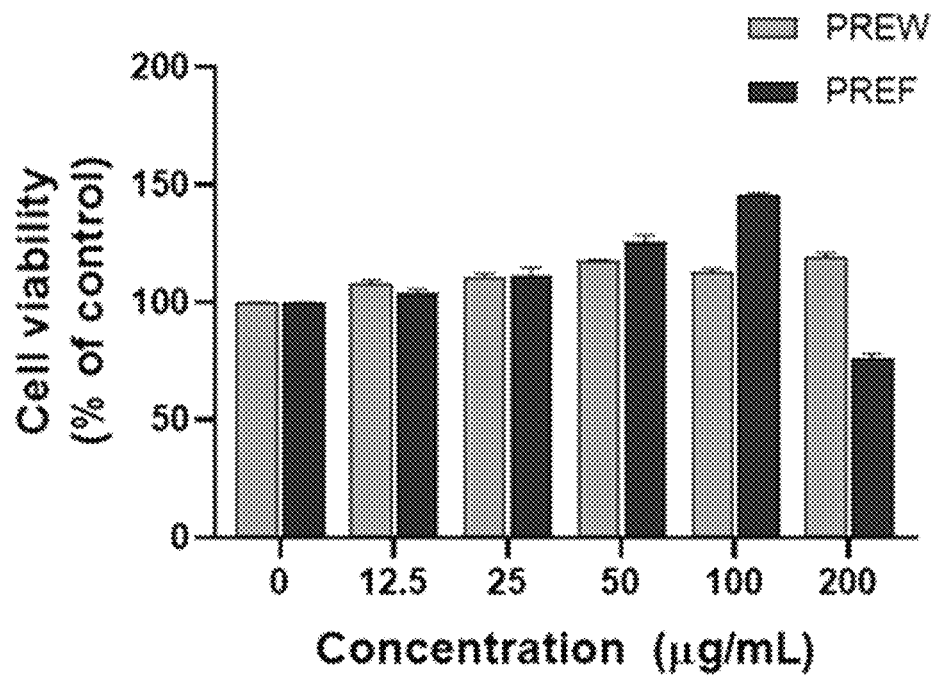
[FIG. 4]
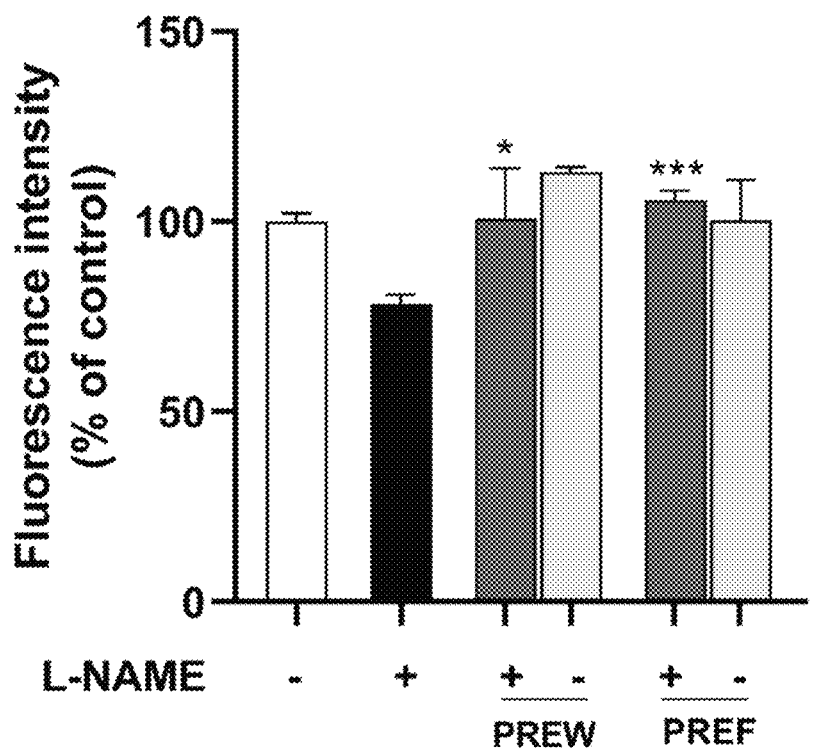

[FIG. 5]
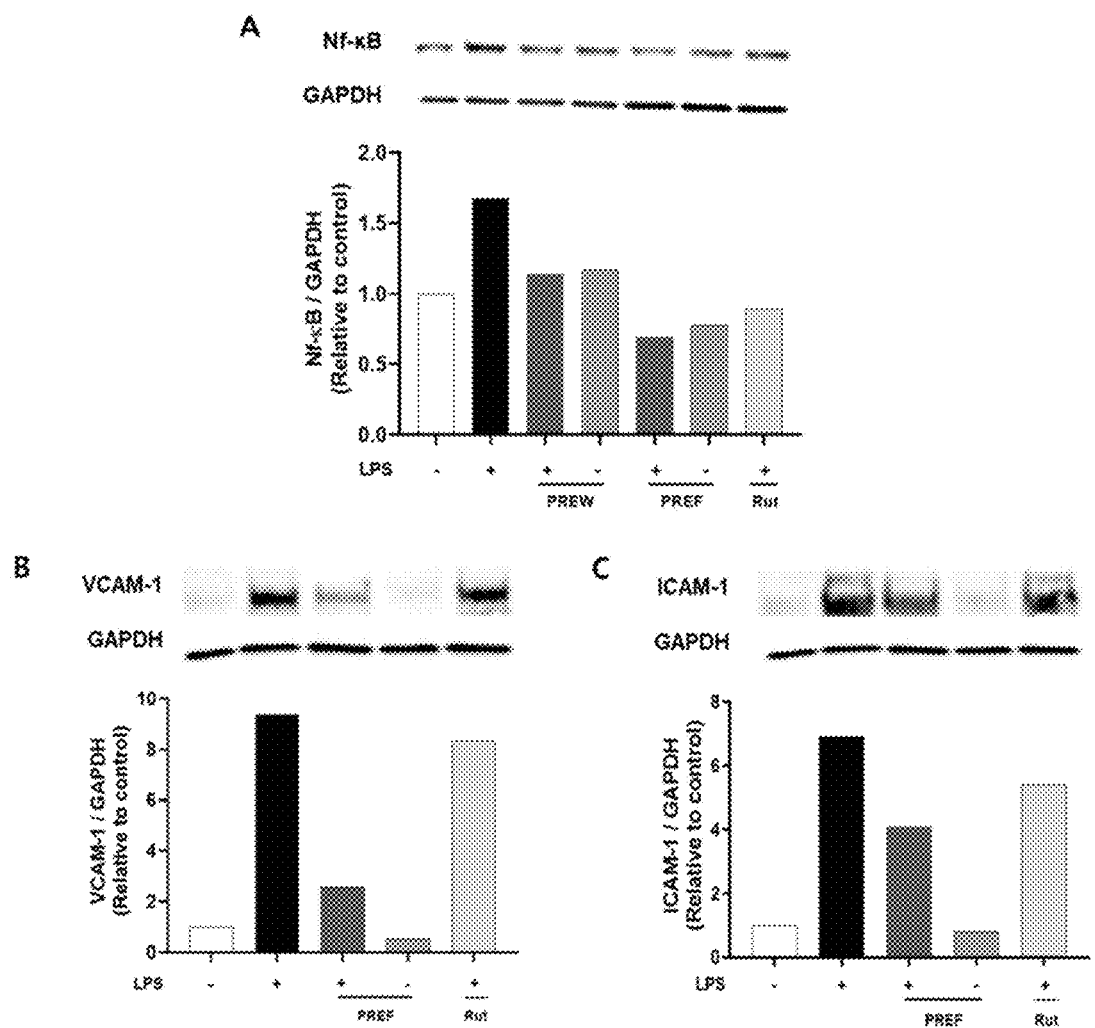

[FIG. 6]
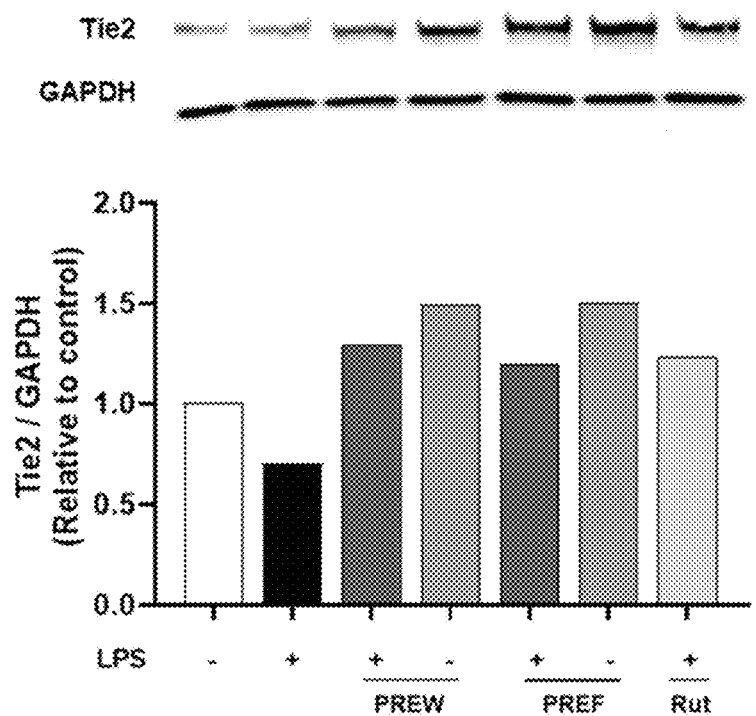
[FIG. 7]
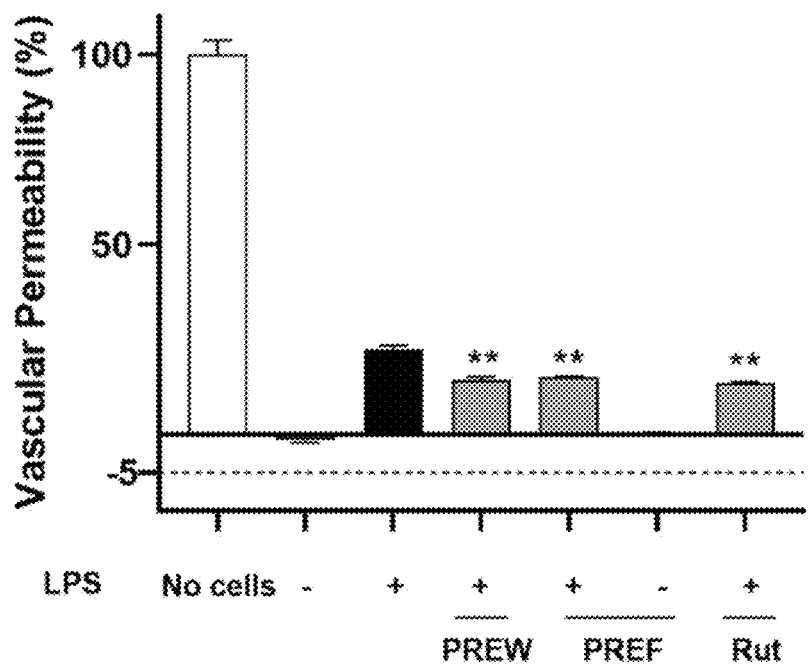

[FIG. 8]
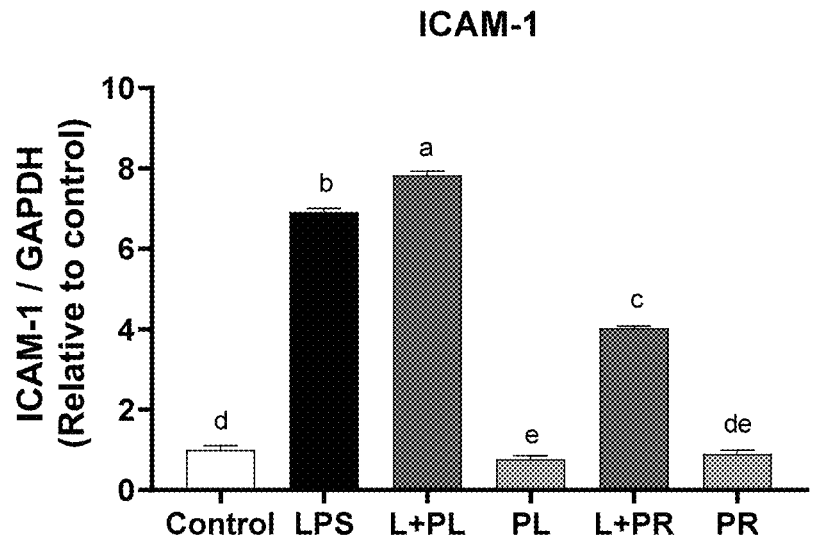
[FIG. 9]
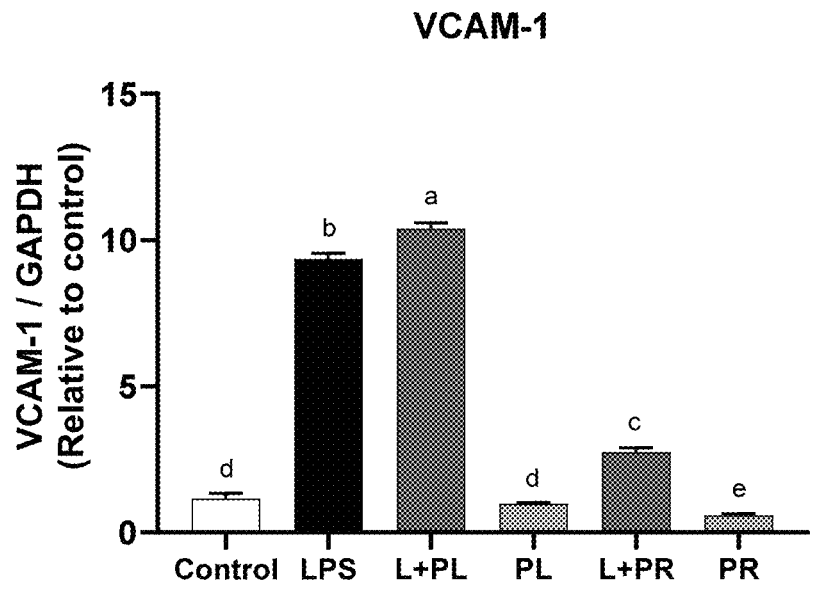

[FIG. 10]
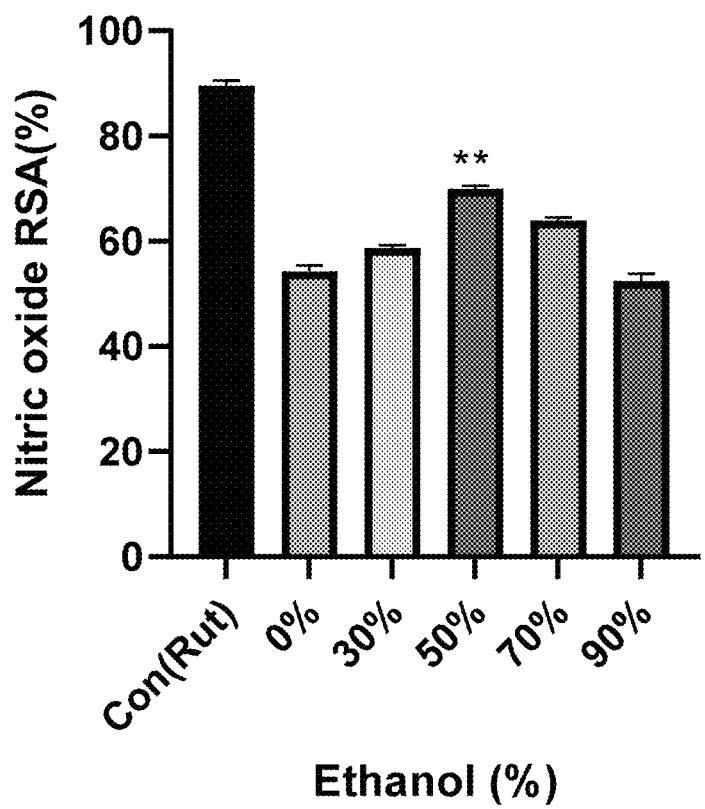
[FIG. 11]
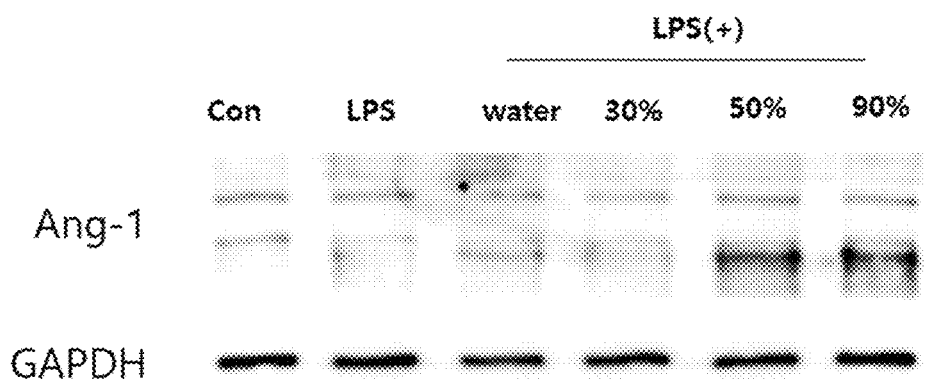

METHOD FOR PREVENTING OR TREATING DISEASES RELATED TO VASCULAR ENDOTHELIAL CELL ACTIVITY REGULATION, COMPRISING A STEP OF ADMINISTERING JAVA PEPPER EXTRACT

TECHNICAL FIELD

The present application relates to a use for prevention, improvement, or treatment of diseases related to vascular dysfunction of Java pepper extract.

BACKGROUND ART

Vascular disease is the second leading cause of death in Korea followed by cancer. When blood vessels are damaged, it may affect heart, brain, and the like, leading to death. The death rate due to vascular disease has been recently increasing more than twice over the past 10 years, and the incidence rate of stroke, myocardial infarction and the like is also rapidly increasing. Cardiocerebrovascular disease is expressed into various symptoms, and acute myocardial infarction or sudden death often appears as the first symptom, so prevention is very important above all else.

Accordingly, development of a substance capable of effectively preventing or treating diseases related to vascular dysfunction is urgent.

DISCLOSURE

Technical Problem

One embodiment of the present application provides a pharmaceutical composition for prevention or treatment of diseases related to vascular dysfunction comprising Java pepper extract as an active ingredient.

Another embodiment of the present application provides a food composition for prevention or improvement of diseases related to vascular dysfunction comprising Java pepper extract.

Other embodiment of the present application provides a use of Java pepper extract for using in prevention, improvement, and/or treatment of diseases related to vascular dysfunction.

Other embodiment of the present application provides a use of Java pepper extract for using in preparation of a composition for prevention, improvement, and/or treatment of diseases related to vascular dysfunction.

Other embodiment of the present application provides a method for prevention, improvement, and/or treatment of diseases related to vascular dysfunction, comprising administering a pharmaceutically effective amount of Java pepper extract into a subject in need of prevention, improvement, and/or treatment of diseases related to vascular dysfunction. The method may further comprise confirming the subject in need of prevention, improvement, and/or treatment of diseases related to vascular dysfunction, before the administering.

Technical Solution

As a result of diligent efforts to develop a composition effective for prevention, improvement, and/or treatment of diseases related to vascular dysfunction, the present application has confirmed that a composition comprising extract of Java pepper (*Piper retrofractum*) has an effect for prevention, improvement, and/or treatment of the diseases, thereby completing the present.

Accordingly, one embodiment of the present application provides Java pepper extract, a use for using in prevention, improvement, and/or treatment of diseases related to vascular dysfunction of the Java pepper extract, and a method for preparation of the Java pepper extract.

Another embodiment of the present application provides a composition for prevention, improvement, and/or treatment of diseases related to vascular dysfunction, comprising the Java pepper extract as an active ingredient. The composition may be a pharmaceutical composition, or food composition.

Other embodiment of the present application provides a use for using in preparation of a composition for prevention, improvement, and/or treatment of diseases related to vascular dysfunction of the Java pepper extract.

Other embodiment of the present invention provides a method for prevention, improvement, and/or treatment of diseases related to vascular dysfunction, comprising administering the Java pepper extract into a subject in need of prevention, improvement, and/or treatment of diseases related to vascular dysfunction.

Hereinafter, the present application will be described in more detail.

Java Pepper Extract

One embodiment of the present application provides Java pepper extract. The Java pepper (*Piper retrofractum* Vahl, *Piper chaba* Hunter, Javanese long pepper, Balinese long pepper, or Cabe Jawa) is one kind of pepper tree fruits, and the pepper tree is an evergreen vine plant belonging to the pepper family, and its origin is Southern India. Dried fruit before maturation is called black pepper, and peeled and dried mature fruit is called white pepper, and it may be powdered or used as a whole, and it may be mainly used as a spice. Java pepper is pepper that is mainly cultivated on Java island and Sumatra island, and may be used by harvesting and drying fruit before ripened. Java pepper has an effect of warming a body and is known to be effective for coughing. The Java pepper used in the present description may be *Piper retrofractum*, and the Java pepper extract used in the present description may be obtained by using a whole plant or part thereof of Java pepper, and the part of Java pepper may be at least one part selected from the group consisting of fruit (for example, at least one selected from the group consisting of flesh, pericarp, seed, and the like), root, stem, leaf, and the like.

The Java pepper extract according to the present application may be obtained by extracting Java pepper, for example, a whole plant of Java pepper or at least one part selected from the group consisting of fruit (for example, at least one selected from the group consisting of flesh, pericarp, seed, and the like), root, stem, leaf, and the like of Java pepper with at least one extraction solvent selected from the group consisting of water and straight chain or branched alcohols having 1 to 4 carbon atoms, and in one embodiment, it may be obtained by extracting with water or an aqueous ethanol solution. The aqueous ethanol solution may mean fermented spirit (fermented ethanol), or may be one obtained by diluting it.

The Java pepper extract according to the present application may be obtained by extracting Java pepper with water or an aqueous ethanol solution of 30 to 100% (v/v), 30 to 90% (v/v), 30 to 80% (v/v), 30 to 70% (v/v), 30 to 60% (v/v), 30 to 50% (v/v), 30 to 40% (v/v), 35 to 100% (v/v), 35 to 90% (v/v), 35 to 80% (v/v), 35 to 70% (v/v), 35 to 60% (v/v), 35 to 50% (v/v), 35 to 40% (v/v), 40 to 100% (v/v), 40 to 90% (v/v), 40 to 80% (v/v), 40 to 70% (v/v), 40 to 60% (v/v), 40 to 50% (v/v), 45 to 100% (v/v), 45 to 90% (v/v), 45 to 80% (v/v), 45 to 70% (v/v), 45 to 60% (v/v), 45 to 50% (v/v), 50 to 100% (v/v), 50 to 95% (v/v), 50 to 90% (v/v), 50 to 85% (v/v), 50 to 80% (v/v), 50 to 75% (v/v), 50 to 70% (v/v), 50 to 65% (v/v), 50 to 60% (v/v), 50 to 55% (v/v), 55 to 100% (v/v), 55 to 95% (v/v), 55 to 90% (v/v), 55 to 85% (v/v), 55 to 80% (v/v), 55 to 75% (v/v), 55 to 70% (v/v), 55 to 65% (v/v), 55 to 60% (v/v), 60 to 100% (v/v), 60 to 95% (v/v), 60 to 90% (v/v), 60 to 85% (v/v), 60 to 80% (v/v), 60 to 75% (v/v), 60 to 70% (v/v), 60 to 65% (v/v), 65 to 100% (v/v), 65 to 95% (v/v), 65 to 90% (v/v), 65 to 85% (v/v), 65 to 80% (v/v), 65 to 75% (v/v), 65 to 70% (v/v), 70 to 100% (v/v), 70 to 95% (v/v), 70 to 90% (v/v), 70 to 85% (v/v), 70 to 80% (v/v), 70 to 75% (v/v), 75 to 100% (v/v), 75 to 95% (v/v), 75 to 90% (v/v), 75 to 85% (v/v), 75 to 80% (v/v), 80 to 100% (v/v), 80 to 95% (v/v), 80 to 90% (v/v), 80 to 85% (v/v), 85 to 100% (v/v), 85 to 95% (v/v), 85 to 90% (v/v), 90 to 100% (v/v), 90 to 95% (v/v), or 95 to 100% (v/v). The aqueous ethanol solution may mean fermented spirit (fermented ethanol, aqueous ethanol solution of 95% (v/v) or more), or may be one obtained by diluting it to regulate the concentration within the above numerical range.

In one embodiment, when the Java pepper extract may be extracted using the extraction solvent, or extracted using an extraction solvent at the above concentration, an effect of prevention, improvement, and/or treatment of diseases related to vascular dysfunction may be more excellent.

In one embodiment, the Java pepper extract may be obtained by extracting Java pepper with water or an aqueous ethanol solution of 40 to 60% (for example, an aqueous solution obtained by diluting fermented spirit at a concentration within the above numerical range.

The content of the extraction solvent added for extracting the Java pepper may be 10 to 100 times, 10 to 75 times, 10 to 50 times, or 10 to 25 times based on the weight of Java pepper, but not limited thereto.

The Java pepper extract according to the present application may be obtained by adjusting pH at the time of extraction, for example, to 5 to 9, 5 to 8.5, 5 to 8, 5 to 7.5, 5 to 7, 5 to 6.5, 5 to 6, 5 to 5.5, 5.5 to 9, 5.5 to 8.5, 5.5 to 8, 5.5 to 7.5, 5.5 to 7, 5.5 to 6.5, 5.5 to 6, 6 to 9, 6 to 8.5, 6 to 8, 6 to 7.5, 6 to 7, 6 to 6.5, 6.5 to 9, 6.5 to 8.5, 6.5 to 8, 6.5 to 7.5, 6.5 to 7, 7 to 9, 7 to 8.5, 7 to 8, 7 to 7.5, 7.5 to 9, 7.5 to 8.5, 7.5 to 8, 8 to 9, 8 to 8.5, or 8.5 to 9, so as to be advantageous for active ingredient content extraction. The pH at the time of extraction may be adjusted by adding a pH adjusting agent together with an extraction solvent into Java pepper. In one embodiment, the pH adjusting agent may be at least one selected from the group consisting of sodium hydroxide, calcium hydroxide, potassium hydroxide, and the like, but not limited thereto, and may be selected from all substances capable of adjusting pH to the above range.

The Java pepper extract according to the present application may be obtained by extracting Java pepper at 50 to 100° C., 50 to 95° C., 50 to 90° C., 50 to 85° C., 50 to 80° C., 50 to 75° C., 50 to 70° C., 50 to 65° C., 50 to 60° C., 50 to 55° C., 55 to 100° C., 55 to 95° C., 55 to 90° C., 55 to 85° C., 55 to 80° C., 55 to 75° C., 55 to 70° C., 55 to 65° C., 55 to 60° C., 60 to 100° C., 60 to 95° C., 60 to 90° C., 60 to 85° C., 60 to 80° C., 60 to 75° C., 60 to 70° C., 60 to 65° C., 65 to 100° C., 65 to 95° C., 65 to 90° C., 65 to 85° C., 65 to 80° C., 65 to 75° C., 65 to 70° C., 70 to 100° C., 70 to 95° C., 70 to 90° C., 70 to 85° C., 70 to 80° C., 70 to 75° C., 75 to 100° C., 75 to 95° C., 75 to 90° C., 75 to 85° C., 75 to 80° C., 80 to 100° C., 80 to 98° C., 80 to 96° C., 80 to 95° C., 80 to 94° C., 80 to 92° C., 80 to 90° C., 80 to 85° C., 85 to 100° C., 85 to 98° C., 85 to 96° C., 85 to 95° C., 85 to 94° C., 85 to 92° C., 85 to 90° C., 90 to 100° C., 90 to 98° C., 90 to 96° C., 90 to 95° C., 90 to 94° C., 90 to 92° C., 92 to 100° C., 92 to 98° C., 92 to 96° C., 92 to 95° C., 92 to 94° C., 94 to 100° C., 94 to 98° C., 94 to 96° C., 94 to 95° C., 95 to 100° C., 95 to 98° C., 95 to 96° C., 96 to 100° C., 96 to 98° C., or 98 to 100° C., but not limited thereto.

The extraction time at the extraction step of Java pepper is sufficient as long as extraction can be sufficiently performed, and may be set to 1 hour or more, 2 hours or more, 3 hours or more, 4 hours or more, or 5 hours or more, or, 1 to 24 hours, 1 to 12 hours, 1 to 6 hours, 1 to 5 hours, 1 to 4 hours, 1 to 3 hours, 1 to 2 hours, 2 to 24 hours, 2 to 12 hours, 2 to 6 hours, 2 to 5 hours, 2 to 4 hours, 2 to 3 hours, 3 to 24 hours, 3 to 12 hours, 3 to 6 hours, 3 to 5 hours, 3 to 4 hours, 4 to 24 hours, 4 to 12 hours, 4 to 6 hours, 4 to 5 hours, 5 to 24 hours, 5 to 12 hours, or 5 to 6 times, or the like, but not limited thereto.

The extraction process used in the method may be performed by all commonly used extraction methods, and for example, it may be performed by at least one method selected from the group consisting of hot water extraction, ultrasonic extraction, reflux extraction, and the like, but not limited thereto. The method may further comprise drying (for example, spray drying, etc.), filtering, and/or concentrating steps of extract as a common method randomly, after the extraction process.

By using the extraction solvent, or extracting under the extraction condition (concentration, temperature, pH and/or extraction time of extraction solvent), the Java pepper extract according to the present application may comprise flavonoids and/or piperine-based alkaloids (amide alkaloids) at a high content.

The Java pepper extract according to the present application may comprise flavonoids at a high content. The flavonoids may be at least one selected form the group consisting of roseoside (Cas No. 54835-70-0), isovitexin-2"-O-glucoside (Cas No. 60767-80-8), vitexin rhamnoside (Cas No. 64820-99-1), and rutin (Cas No. 153-18-4).

The Java pepper extract according to the present application may comprise piperine-based alkaloids at a high content. The piperine-based alkaloids may be at least one selected form the group consisting of piperine (Cas No. 94-62-2), piperchabaoside B (PubChem CID No. 44521607), piperlongumine (Cas No. 20069-09-4), piperyline (Cas No. 25924-78-1), piperanine (Cas No. 23512-46-1), dihydropiperlonguminine (Cas No. 23512-53-0), piperlonguminine (Cas No. 5950-12-9), piperdardine (PubChem CID No. 10086948), pellitorine (Cas No. 18836-52-7), pipercallosine (PubChem CID No. 5372201), dehydropipernonaline (Cas No. 107584-38-3), pipernonaline (Cas No. 88660-10-0), retrofractamide B (or pipercide, Cas No. 54794-74-0), piperolein B (Cas No. 30505-89-6), N-isobutyl-2,4,-dodecadienamide (Cas No. 24738-51-0), piperundecalidine (Cas No. 88660-11-1), piperchabamide B (PubChem CID No. 44453655), guineensine (Cas No. 55038-30-7), piperchabamide C (PubChem CID No. 44454018), N-isobutyl-2,4,12-octadecatrienamide (Cas No. 151391-69-4), 1-(2,4, 12-octadecatrienoyl)piperidine (Cas No. 151391-71-8), and N-isobutyl-2,4,14-eicosatrienamide (Cas No. 151391-70-7). In one embodiment, the piperine-based alkaloid may be piperine.

In the present description, specific compound names, structures, and the like of the flavonoids and/or piperine-based alkaloids (amide alkaloids) comprised in the Java pepper extract may be confirmed on a known search site (pubchem or commonchemistry.cas, etc.).

The content of the flavonoids and/or piperine-based alkaloids (for example, piperine) comprised in the Java pepper extract according to the present application, may be 1 to 1000 mg/g, 1 to 900 mg/g, 1 to 800 mg/g, 1 to 700 mg/g, 1 to 600 mg/g, 1 to 500 mg/g, 1 to 400 mg/g, 1 to 300 mg/g, 1 to 200 mg/g, 1 to 100 mg/g, 50 to 1000 mg/g, 50 to 900 mg/g, 50 to 800 mg/g, 50 to 700 mg/g, 50 to 600 mg/g, 50 to 500 mg/g, 50 to 400 mg/g, 50 to 300 mg/g, 50 to 200 mg/g, 50 to 100 mg/g, 100 to 1000 mg/g, 100 to 900 mg/g, 100 to 800 mg/g, 100 to 700 mg/g, 100 to 600 mg/g, 100 to 500 mg/g, 100 to 400 mg/g, 100 to 300 mg/g, 100 to 200 mg/g, 150 to 1000 mg/g, 150 to 900 mg/g, 150 to 800 mg/g, 150 to 700 mg/g, 150 to 600 mg/g, 150 to 500 mg/g, 150 to 400 mg/g, 150 to 300 mg/g, or 150 to 200 mg/g, based on the solid weight (g) of the Java pepper extract, but not limited thereto. The piperine (CAS NO. 94-62-2) may be a compound having the structure of Chemical formula 1 below.

[Chemical formula 1]

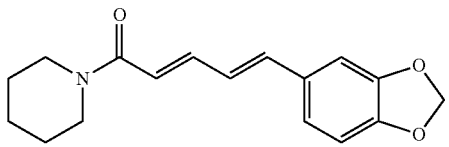

The Java pepper extract according to the present application may have various advantageous activities such as activating ability of vascular endothelial cells, improving ability of vascular contraction and relaxation function, reducing ability of vascular endothelial cell attachment factor expression, vascular anti-inflammatory efficacy, reinforcing ability of vascular endothelial binding capacity, reducing ability of vascular permeability, activity to stabilize blood vessels, activity to promote maturation of blood vessels, normalizing activity of blood vessels, and the like for blood vessels.

In one embodiment, the Java pepper extract according to the present application may have an anti-inflammatory activity, and/or an activity of prevention, improvement, and/or treatment of diseases related to vascular dysfunction, due to the advantageous activities as above.

In the present description, the term "anti-inflammatory activity" may mean all activities which reduce inflammation such as inhibiting inflammation occurrence, or alleviating the degree of inflammation, and the like. In one embodiment, the anti-inflammatory activity may mean an activity of inhibiting proliferation of inflammatory cells (for example, macrophages, etc.) causing inflammation or inhibiting gene transcription or inhibiting protein translation of inflammatory substances (for example, inflammatory cytokines, histamine, etc.) produced by inflammatory cells. In one embodiment, the anti-inflammatory activity may mean reducing inflammatory substances produced by an immune response (for example, nuclear factor κB (NF-κB, nuclear factor kappa-light-chain-enhancer of activated B cells), intracellular adhesion molecule-1 (ICAM(Intercellular Adhesion Molecule)-1), and/or vascular cell adhesion molecule 1 (VCAM-1), etc.). The inflammation may be inflammation occurring in blood vessels, and/or be caused by diseases related to vascular dysfunction.

In the present description, the term "diseases related to vascular dysfunction" may be diseases caused by malfunction of vascular endothelial cells, vascular contraction and relaxation malfunction, vascular inflammatory responses, and/or vascular permeability increase.

In other words, the Java pepper extract provided in the present application has an excellent effect in prevention, improvement, and/or treatment of diseases related to vascular dysfunction. The diseases related to vascular dysfunction may be at least one selected from the group consisting of inflammation (for example, inflammation occurring in blood vessels, or inflammation due to diseases related to vascular dysfunction, etc.), oedema, capillary leak syndrome, hyperlipidemia, hypertriglyceridemia, cerebrovascular disease, renovascular disease, peripheral vascular disease, vasculitis, aneurysm, thrombosis or embolism (for example, stroke, pulmonary embolism, myocardial infarction, arterial thrombosis, venous thrombosis, portal vein thrombosis, pulmonary arterial embolism, deep vein thrombosis), arteriosclerosis (for example, arteriosclerosis due to diabetes), small vessel disease (for example, small vessel disease due to diabetes), limb ischemia, gangrene (for example, dry gangrene or wet gangrene), Buerger's disease), Raynaud disease (Raynaud'S Phenomenon), hand-foot syndrome (Hand-Arm Vibration Syndrome, HAVS), varices (for example, varicose vein), and superficial thrombophlebitis.

In the present description, the term "blood vessel" may mean at least one region selected from the group consisting of arteries, veins and capillaries (microvessels). Therefore, the diseases related to vascular dysfunction may mean diseases related to arterial dysfunction, diseases related to venous dysfunction, and/or diseases related to capillary dysfunction. In other words, it may include diseases occurring synthetically as function of at least one region selected from the group consisting of arteries, veins and capillaries is degraded together. For example, it may include diseases caused by dysfunction of peripheral blood vessels (at least one blood vessel selected from the group consisting of peripheral arteries, peripheral veins, and peripheral capillaries) of a specific body part such as a hand or foot (for example, gangrene (for example, dry gangrene, or wet gangrene), Buerger's disease, Raynaud's disease (Raynaud'S Phenomenon), hand-foot syndrome (Hand-Arm Vibration Syndrome, HAVS), etc.).

Arteries are known to have well-developed elastic fibers and smooth muscles, so they are rich in elasticity and allow blood to flow with its own elasticity, even when the vascular lumen is widened by blood pressure. During this process, due to contraction of smooth muscles, resistance to blood flow occurs, and blood pressure rises due to resistance, which is the process of causing hypertension. Diseases related to arterial dysfunction may be at least one selected from the group consisting of hypertension, aneurysm, ischemic heart disease, coronary artery disease, angina, myocardial infarction, atherosclerosis, stroke, intracerebral bleeding, cerebral infarction, arrhythmia, arteriosclerosis (for example, arteriosclerosis due to diabetes), inflammation occurring in arteries, arterial hyperlipidemia, arterial hypertriglyceridemia, arterial cerebrovascular disease, arterial renovascular disease, arterial vasculitis, arterial thrombosis (or arterial embolism, for example, pulmonary embolism, etc.), small arterial vascular diseases, gangrene (for example, dry gangrene, or wet gangrene), Buerger's disease, Raynaud's disease (Raynaud'S Phenomenon), hand-foot syndrome (Hand-Arm Vibration Syndrome, HAVS) and the like. The diseases related to arterial dysfunction may occur in brain and/or heart, and the like.

Veins are known to have fewer elastic fibers and many connective tissues, so it has less elasticity than arteries. Therefore, although blood may pool or flow backwards under the influence of gravity, but a venous valve (valve) is located in the lumen plays a role of preventing backflow of blood. Diseases related to venous dysfunction may be at least one selected from the group consisting of varices (for example, varicose veins, etc.), oedema, venous insufficiency (for example, chronic venous insufficiency (CVI)), deep vein thrombosis, phlebitis, spider veins, venous hyperlipidemia, venous hypertriglyceridemia, venous cerebrovascular disease, venous renovascular disease, venous thrombosis (or venous embolism, for example, pulmonary venous embolism, etc.), pulmonary venous vascular disease, gangrene (for example, dry gangrene or wet gangrene), Buerger's disease, Raynaud's disease (Raynaud'S Phenomenon), hand-foot syndrome (Hand-Arm Vibration Syndrome, HAVS), and the like, but not limited thereto. The diseases related to venous dysfunction may occur in the lower body, and the like.

Capillaries are known to be composed of endothelial cell layers without myocytes and connective tissue, and have a structure convenient for exchanging substances in and out of blood vessels, but have a disadvantage in that they are vulnerable to external stress. Exchange of substances in capillaries occurs due to a concentration difference and a pressure difference. As there is a pressure difference between blood and tissue fluid in capillaries, the pressure of blood is high in capillaries on the arterial side, so moisture flows out of blood vessels from inside of the blood vessels, and the pressure of tissue fluid is high in capillaries on the venous side, so moisture is absorbed into blood vessels from the outside. Diseases related to capillary dysfunction may be at least one selected from the group consisting of hereditary haemorrhagic telangiectasia, systemic capillary leak syndrome, glomerulonephritis, gangrene (for example, dry gangrene or wet gangrene), Buerger's disease, Raynaud's disease (Raynaud'S Phenomenon), hand-foot syndrome (Hand-Arm Vibration Syndrome, HAVS), and the like, but not limited thereto. The diseases related to capillary dysfunction may occur in skin, eyes, and/or kidney, and the like.

The Java pepper extract according to the present application may exhibit an anti-inflammatory activity, and/or an activity of prevention, improvement, and/or treatment of diseases related to vascular dysfunction, without addition of other components, but it may be used together with a commonly used component for conveniently treating, administering, or ingesting the Java pepper extract. For example, the Java pepper extract may comprise a commonly used excipient, additive, or the like additionally, to formulate (prepare) the Java pepper extract, and for example, it may additionally comprise dextrin. The dextrin may mean a low molecular weight carbohydrate produced by hydrolysis of starch. The dextrin $(C_6H_{10}O_5)_n$, n may be a natural number of 1 or more, for example, n may be a natural number of 10,000 or less, 1,000 or less, or 100 or less.) is a polysaccharide in a form of polymerizing several sugars as Chemical formula 2 below.

In the present description, the Java pepper extract may be used as a meaning of encompassing Java pepper extract alone, or Java pepper extract additionally comprising a component (for example, dextrin, etc.) commonly used to formulate Java pepper extract, and in one embodiment, the Java pepper extract additionally comprising a component commonly used to formulate Java pepper extract may be described as "complex of Java pepper extract". In one embodiment, the complex of Java pepper extract may mean comprising Java pepper extract and dextrin.

[Chemical formula 2]

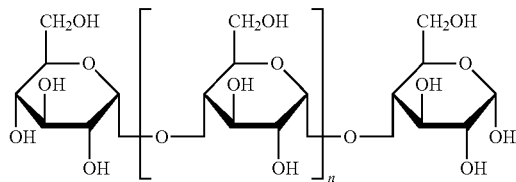

The mixing ratio of the Java pepper extract and dextrin comprised in the complex of the Java pepper extract may be 1:10 to 0.1, 1:10 to 0.111 (or, 1:10 to 9:1), 1:10 to 0.125, 1:10 to 0.142857 (or, 1:10 to 7:1), 1:10 to 0.167 (or, 1:10 to 6:1), 1:10 to 0.2, 1:10 to 0.25, 1:10 to 0.333 (or, 1:10 to 3:1), 1:10 to 0.5, 1:10 to 1, 1:10 to 2, 1:10 to 3, 1:10 to 4, 1:10 to 5, 1:10 to 6, 1:10 to 7, 1:10 to 8, 1:10 to 9, 1:9 to 0.1, 1:9 to 0.111 (or, 1:9 to 9:1), 1:9 to 0.125, 1:9 to 0.142857 (or, 1:9 to 7:1), 1:9 to 0.167 (or, 1:9 to 6:1), 1:9 to 0.2, 1:9 to 0.25, 1:9 to 0.333 (or, 1:9 to 3:1), 1:9 to 0.5, 1:9 to 1, 1:9 to 2, 1:9 to 3, 1:9 to 4, 1:9 to 5, 1:9 to 6, 1:10 to 7, 1:9 to 8, 1:8 to 0.1, 1:8 to 0.111 (or, 1:8 to 9:1), 1:8 to 0.125, 1:8 to 0.142857 (or, 1:8 to 7:1), 1:8 to 0.167 (or, 1:8 to 6:1), 1:8 to 0.2, 1:8 to 0.25, 1:8 to 0.333 (or, 1:8 to 3:1), 1:8 to 0.5, 1:8 to 1, 1:8 to 2, 1:8 to 3, 1:8 to 4, 1:8 to 5, 1:8 to 6, or 1:10 to 7 (solid weight of concentrate of Java pepper extract: dextrin weight), based on the solid weight (g) of concentrate of the Java pepper extract, but not limited thereto.

In one embodiment, the mixing ratio of Java pepper extract and dextrin comprised in the complex of Java pepper extract, may be 1:9, 1:2.33 (or 3:7), or 1:1 (solid weight of concentrate of Java pepper extract: dextrin weight), based on the solid weight (g) of concentrate of the Java pepper extract, but not limited thereto.

The solid weight means the weight of solids remaining after removing a solvent component of extract. This is a term used to show that the mixing ratio means a ratio between component weights in which an extraction solvent is removed so as to be unaffected by phase and/or concentration of extract, in case in that the mixture is a mixture of Java pepper extract and dextrin. In the present description, as above, the complex of Java pepper extract comprising Java pepper extract and dextrin, may be interchangeably used with "Java pepper extract".

Use of Java Pepper Extract

Other embodiment of the present application provides a use for using Java pepper extract in prevention, improvement, and/or treatment of diseases related to vascular dysfunction.

Other embodiment provides a composition for prevention, improvement, and/or treatment of diseases related to vascular dysfunction comprising Java pepper extract as an active ingredient. The composition may be a pharmaceutical composition, or food composition.

Other embodiment provides a use for using Java pepper extract in preparation of a composition for prevention, improvement, and/or treatment of diseases related to vascular dysfunction.

In the present description, "prevention" may mean any action that inhibits or delays onset of diseases (disorders) by administration of the composition according to one embodiment, and "treatment" may mean any action that improves or beneficially changes symptoms of suspected and affected subjects of diseases by administration of the composition according to one embodiment, and "improvement" may mean any action that at least reduces a parameter related to a condition in which diseases are treated by administration of the composition according to one embodiment, for example, the severity of symptoms. The disease may be diseases related to vascular dysfunction.

One embodiment provides a pharmaceutical composition for prevention, improvement, and/or treatment of diseases related to vascular dysfunction comprising Java pepper extract as an active ingredient.

Another embodiment provides a method for prevention, improvement, and/or treatment of diseases related to vascular dysfunction, comprising administering a pharmaceutically effective dose of Java pepper extract into a subject in need of prevention, improvement and/or treatment of diseases related to vascular dysfunction. The method may further comprise confirming a subject in need of prevention, improvement and/or treatment of diseases related to vascular dysfunction, before the administering.

The Java pepper extract comprised or used in the composition and/or method provided in the present description is as described above.

The administration method of the pharmaceutical composition according to one embodiment is not limited as long as it can reach target tissue. For example, it may be parenteral administration such as intra-abdominal administration, intraperitoneal injection, intra-articular injection, intra-arterial injection, intravenous injection, dermal administration (for example, application to skin), dermal injection, local application, intramuscular administration, intraperitoneal administration, or oral administration, but not limited thereto. In addition, the pharmaceutical composition may be administered by any device allowing an active substance to move to a target cell.

The pharmaceutical composition according to one embodiment may further comprise an appropriate carrier, excipient or diluent commonly used in preparation of pharmaceutical compositions. Specifically, the pharmaceutical composition may be used as formulated in a form of oral formulations such as powder, granules, tablets, capsules, suspension, emulsion, syrup, aerosols, and the like, external preparation, suppository and sterile injection solution according to a common method, respectively. The carrier, excipient and diluent which can be comprised in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. When formulated, it is prepared using a diluent or excipient such as commonly used fillers, thickeners, binders, wetting agents, disintegrating agents, surfactants, and the like. Solid preparations for oral administration include tablets, pills, powders, granules, capsules, and the like, and these solid preparations are prepared by mixing at least one excipient, for example, starch, calcium carbonate, sucrose or lactose, gelatin, and the like to the composition. In addition, other than simple excipients, lubricants such as magnesium stearate, talc and the like are used. Suspension, oral liquids, emulsion, syrup and the like correspond to liquid preparations for oral administration, and in addition to commonly used simple diluents, water and liquid paraffin, various excipients, for example, wetting agents, sweeteners, flavoring agents, preservatives, and the like may be comprised. Preparations for parenteral administration includes sterilized aqueous solutions, non-aqueous solvents, suspension, emulsion, lyophilized preparations, and suppositories. As the non-aqueous solvents and suspension, propylene glycol, polyethylene glycol, vegetable oil such as olive oil, injectable ester such as ethyl oleate, and the like may be used. As a base of suppositories, witepsol, macrogol, tween 61, cacao butter, laurin butter, glycerogelatin, and the like may be used.

The pharmaceutical composition according to one embodiment may be administered in a pharmaceutically effective dose, and in the present application, "pharmaceutically effective dose" means an amount sufficient for treating or preventing diseases at a reasonable benefit/risk ratio applicable to medical treatment or prevention, and the effective dose level may be determined according to factors including the severity of disease, activity of a drug, patient's age, body weight, health, gender, patient's sensitivity to a drug, administration hour, administration route and excretion ratio of the used composition of the present application, treatment period, a drug mixed or simultaneously used with the used composition of the present application and other factors well known in the medical field. The pharmaceutical composition according to one embodiment may be administered as an individual therapeutic agent, or be administered in combination with another therapeutic agent, or be administered in order or simultaneously with a conventional therapeutic agent. In addition, it may be under single or multiple administration. It is important to administer an amount capable of obtaining a maximal effect with a minimal amount without side effects considering all the above factors.

The dose of the pharmaceutical composition according to one embodiment, may be administered, for example, at 0.0001 to 10,000 mg/g, 0.0001 to 5,000 mg/g, 0.0001 to 1,000 mg/g, 0.0001 to 500 mg/g, 0.0001 to 100 mg/g, 0.0001 to 50 mg/g, 0.0001 to 10 mg/g, 0.001 to 10,000 mg/g, 0.001 to 5,000 mg/g, 0.001 to 1,000 mg/g, 0.001 to 500 mg/g, 0.001 to 100 mg/g, 0.001 to 50 mg/g, 0.001 to 10 mg/g, 0.01 to 10,000 mg/g, 0.01 to 5,000 mg/g, 0.01 to 1,000 mg/g, 0.01 to 500 mg/g, 0.01 to 100 mg/g, 0.01 to 50 mg/g, 0.01 to 10 mg/g, 0.1 to 10,000 mg/g, 0.1 to 5,000 mg/g, 0.1 to 1,000 mg/g, 0.1 to 500 mg/g, 0.1 to 100 mg/g, 0.1 to 50 mg/g, 0.1 to 10 mg/g, 1 to 10,000 mg/g, 1 to 5,000 mg/g, 1 to 1,000 mg/g, 1 to 500 mg/g, 1 to 100 mg/g, 1 to 50 mg/g, or 1 to 10 mg/g to a mammal for a day, but not limited thereto. The administration frequency of the pharmaceutical composition of the present application is not particularly limited thereto, but it may be administered once a day, or be administered several times by dividing the dose. The dose is not intended to limit the scope of the present application in any way.

The administration subject of the pharmaceutical composition provided in the present description may be a mammal including humans, dogs, cats, horses, cows, pigs, goats, rabbits, mice, rats, and the like, or a cell or tissue derived therefrom or culture thereof, and in one embodiment, the subject may be a subject (mammal such as humans, etc.) in need of prevention, improvement, and/or treatment of diseases related to vascular dysfunction as described above, or with disease related to vascular dysfunction, or a cell or tissue isolated therefrom, or culture thereof.

The pharmaceutical composition according to one embodiment may comprise the Java pepper extract by 1 to 80% by weight, 5 to 80% by weight, 5 to 75% by weight, 5 to 70% by weight, 5 to 65% by weight, 50 to 70% by weight, 55 to 65% by weight, 60 to 65% by weight, 10 to 60% by weight, 15 to 60% by weight, 20 to 60% by weight, 1 to 50% by weight, 5 to 50% by weight, 10 to 50% by weight, 15 to 50% by weight, 20 to 50% by weight, 1 to 40% by weight, 5 to 40% by weight, 10 to 40% by weight, 15 to 40% by weight, 20 to 40% by weight, 1 to 30% by weight, 5 to 30% by weight, 10 to 30% by weight, 15 to 30% by weight, 20 to 30% by weight, 1 to 25% by weight, 5 to 25% by weight, 10 to 25% by weight, 15 to 25% by weight, 20 to 25% by weight, or 23 to 25% by weight.

One embodiment provides a food composition for prevention, and/or improvement of diseases related to vascular dysfunction comprising Java pepper extract.

The food composition according to one embodiment may mean meat, sausage, bread, chocolate, candies, snacks, confectionery, pizza, ramen, other noodles, gum, dairy products including ice cream, various kinds of soup, beverages, tea, drinks, alcohol beverages, vitamin complexes, health functional foods and health foods and the like, and includes all foods in a conventional sense.

The health functional food is the same term as food for special health use (FoSHU), and means food with high medical science and medical effects processed to efficiently exhibit body modulating function in addition to nutrition supply. The health food means food having an effect of active health maintenance or enhancement compared to general food, and health supplement food means food for a purpose of health supplement. In some cases, the terms of health functional food, health food, and health supplement food may be interchangeably used. Herein, "function" means obtaining useful effects for health purposes such as regulating nutrients or physiological actions for the structure and function of the human body. The food of the present application can be prepared by a method commonly used in the art, and during preparation, it may be prepared by adding a raw material and a component commonly added in the art. In addition, the formulation of the food may be also prepared without limitation as long as the formulation is recognized as food. The food composition of the present application may be prepared in various types of formulations, and has an advantage that there is no side effect that may occur in case of long-term use as it uses food as a raw material differently from general drugs, and it is excellent in portability, so the food composition of the present application can be ingested as an adjuvant to enhance an effect of prevention or improvement of diseases related to vascular dysfunction.

Specifically, the health functional food is what is obtained by adding the composition according to one embodiment into food materials such as beverages, tea, spice, gum, confectionery, and the like, or is prepared by encapsulation, powdering, suspension, or the like, and refers to that it brings a specific effect on health when this is ingested, but there is an advantage that there is no side effect that may occur when taking a drug for a long period of time using food as a raw material differently from general drugs.

The food composition according to one embodiment, can be daily ingested, and therefore, a high effect on prevention or improvement of diseases related to vascular dysfunction can be expected, so it can be very usefully used.

The food composition may further comprise a physiologically acceptable carrier, and the type of the carrier is not particularly limited, and any carrier commonly used in the corresponding technical field may be used.

In addition, the food composition may comprise an additional component capable of improving odor, taste, view, and the like by being commonly used in a food composition. For example, it may comprise vitamins A, C, D, E, B1, B2, B6, B12, niacin, biotin, folate, panthotenic acid, and the like. In addition, it may comprise minerals such as zinc (Zn), iron (Fe), calcium (Ca), chrome (Cr), magnesium (Mg), manganese (Mn), copper (Cu), chrome (Cr), and the like. In addition, it may comprise amino acids such as lysine, tryptophan, cysteine, valine, and the like.

In addition, the food composition may comprise food additives such as preservatives (potassium sorbate, sodium benzoate, salicylic acid, sodium dehydroacetate, etc.), sterilizers (bleaching powder and high-grade bleaching powder, sodium hypochlorite, etc.), anti-oxidants (butylhydroxyanisole (BHA), butylhydroxytoluene (BHT), etc.), coloring agents (tar color, etc.), color developing agents (sodium nitrite, sodium nitrous acid, etc.), bleaching agents (sodium sulfite), seasoning (MSG sodium glutamate, etc.), sweeteners (dulcin, cyclamate, saccharin, sodium, etc.), spice (vanillin, lactones, etc.), expanding agents (alum, D-potassium hydrogen tartrate, etc.), reinforcing agents, emulsifiers, thickeners, coating agents, gum bases, defoaming agents, solvents, improving agents, and the like. The additive may be selected depending on the type of food and be used in an appropriate amount.

The composition according to one embodiment may be added as it is or be used together with other food or food component, and may be appropriately used according to a common method. The mixed amount of the active ingredient may be appropriately determined according to purpose for use thereof (prevention, health or therapeutic treatment). In general, at the time of preparation of a food or beverage, the food composition of the present application may be added in an amount of 50 parts by weight or less, specifically, 20 parts by weight or less, based on the food or beverage. However, when ingesting for a long period of time on a purpose of health and hygiene, the content in the above range or less may be comprised, and there was not any problem in the aspect of safety, so the active ingredient may be used also in an amount in the above range or more.

As one embodiment of the food composition, it may be used as a beverage composition, and in this case, various flavoring agents or natural carbohydrates, or the like may be contained as an additional component as same as common beverages. The afore-mentioned natural carbohydrates may be monosaccharides such as glucose, fructose; disaccharides such as maltose, sucrose; polysaccharides such as dextrin, cyclodextrin; or sugar alcohols such as xylitol, sorbitol, erythritol, and the like. As a sweetener, natural sweeteners such as thaumatin, *stevia* extract; synthetic sweeteners such as saccharin and aspartame and the like. The ratio of the natural carbohydrates may be generally about 0.01 to 0.04 g, specifically, about 0.02 to 0.03 g, per 100 ml of the health beverage composition of the present application.

In addition to the above, the health beverage composition may contain various nutritional supplements, vitamins, electrolytes, flavoring agents, coloring agents, pectic acid, salts of pectic acid, alginic acid, salts of alginic acid, organic acid, protective colloidal thickeners, pH adjusting agents, stabilizers, preservatives, glycerin, alcohols, or carbonating agents, or the like. It may contain flesh for preparation of natural fruit juices, fruit juice beverages, or vegetable beverages in addition thereto. These components may be used independently or in combination. The ratio of these additives is not significantly important, but it is common as selected in a rage of 0.01 to 0.1 part by weight per 100 parts by weight of the health beverage composition of the present application.

The food composition according to one embodiment may be comprised by various % by weights, as long as it can exhibit an effect of prevention or improvement of diseases related to vascular dysfunction, but for example, the composition according to one embodiment may be comprised by 0.00001 to 100% by weight or 0.01 to 80% by weight based on the total weight of the food composition, but not limited thereto.

Other embodiment provides a method for preparation of the Java pepper extract.

The method for preparation of the Java pepper extract, may comprise extracting Java pepper with an extraction solvent.

The extraction process used in the method may be performed by all commonly used extraction methods, and for example, may be performed by at least one method selected from the group consisting of hot water extraction, ultrasonic extraction, reflux extraction method, and the like, but not limited thereto. The method may further comprise drying (for example, spray drying, etc.), filtering, and/or concentrating steps of extract as a common method randomly, after the extraction process.

The contents of the extraction condition such as the extraction solvent, extraction temperature, extraction time, and the like are same as described above.

Advantageous Effects

The composition comprising Java pepper extract according to the present application, has an excellent anti-inflammatory effect, and has an excellent effect of prevention, improvement, and/or treatment of diseases related to vascular dysfunction, while having excellent biosafety.

BRIEF DESCRIPTION OF THE DRAWINGS

FIG. 2a and FIG. 2b are graphs of confirming flavonoid and piperine-based alkaloid components comprised in the hot water extract (FIG. 2a) and fermented spirit extract (FIG. 2b) of Java pepper according to the present application.

FIG. 3 is a graph of confirming the viability of vascular endothelial cells (HDMECs cells, hereinafter, same), when the hot water extract (PREW) and fermented spirit extract (PREF) of Java pepper according to the present invention are treated, respectively.

FIG. 4 shows the produced amount of nitrogen monoxide in vascular endothelial cells, when the hot water extract (PREW) and fermented spirit extract (PREF) of Java pepper according to the present invention are treated into the vascular endothelial cells, respectively, as a graph.

FIG. 5 shows the expression level of inflammatory factor proteins (Nf-κB, ICAM-1 and VCAM-1) in vascular endothelial cells, when an inflammation inducing material, LPS is treated (LPS(+)) or not treated (LPS(−)), and the hot water extract (PREW) and fermented spirit extract (PREF) of Java pepper according to the present invention are treated into the vascular endothelial cells, respectively, as a graph. Rut means a positive control group (rutin treatment).

FIG. 6 shows the expression level of vascular endothelial binding capacity reinforcement factor protein (Tie2 protein) in vascular endothelial cells, when an inflammation inducing material, LPS is treated (LPS(+)) or not treated (LPS(−)), and the hot water extract (PREW) and fermented spirit extract (PREF) of Java pepper according to the present invention are treated into the vascular endothelial cells, respectively, as a graph. Rut means a positive control group (rutin treatment).

FIG. 7 shows the transmittance by measuring vascular permeability of vascular endothelial cells, when an inflammation inducing material, LPS is treated (LPS(+)) or not treated (LPS(−)), and the hot water extract (PREW) and fermented spirit extract (PREF) of Java pepper according to the present invention are treated into the vascular endothelial cells, respectively, as a graph. Rut means a positive control group (rutin treatment).

FIG. 8 and FIG. 9 show that Java pepper extract reduces the expression level of the inflammation inducing material, but Long pepper extract belonging to a congeneric plant shows rather an opposite effect, in the LPS-treated HDMECs cells.

FIG. 10 is a graph showing that the effect of inhibiting production of excessive nitrogen monoxide of the Java pepper extract obtained by extracting Java pepper with a 50% aqueous ethanol solution is more excellent.

FIG. 11 shows that the Java pepper extract obtained by extracting Java pepper with a 50% aqueous ethanol solution significantly increases the Ang-1 protein expression level.

MODE FOR INVENTION

Hereinafter, the present invention will be described in more detail by the following examples. However, they are intended to illustrate the present invention only, but the scope of the present invention is not limited by these examples.

Example 1. Preparation of Complex of Java Pepper Extract

Figure 1:
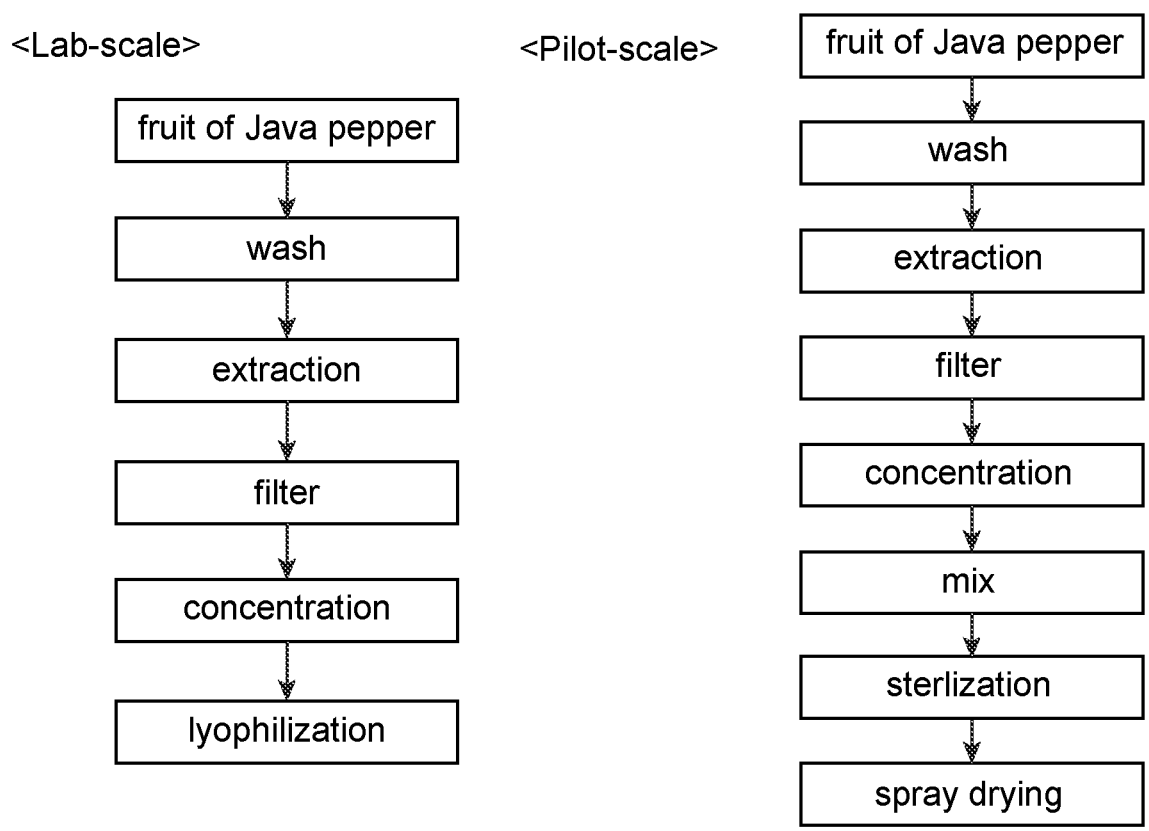
FIG. 1 shows a schematic diagram of the method for preparation of Java pepper extract according to the present application. The left (lab-scale) of FIG. 1 is freeze-drying Java pepper extract, and the right (pilot-scale) of FIG. 1 is mixing and spray drying Java pepper extract and dextrin.

The entire preparation method of the complex of Java pepper extract (mixture of Java pepper extract and dextrin) is showed as a schematic diagram (right of FIG. 1, pilot-scale) in FIG. 1.

1) Fruits of Java pepper (Java pepper was acquired (purchased) from CK Co., Ltd.) were washed and dried.
2) The dried Java pepper fruits were extracted by heating under the temperature condition of 70° C. for 5 hours, respectively, using hot water (~100° C.) and 50% (v/v) fermented spirit.
3) The extract was filtered with a filter with a diameter of 50 μm to obtain a filtrate.
4) The filtrate was concentrated under reduced pressure at 60° C. based on 10% solids to obtain a concentrated solution of Java pepper extract.
5) Java pepper and dextrin (dextrin was acquired (purchased) from CK Co., Ltd.) were mixed at a ratio of 1:9, 3:7 or 5:5, based on the solid content of the concentrated solution of Java pepper extract obtained in the step 4).
6) Sterilization was performed for 3 kinds of mixtures obtained in the step 5) at 80~85° C. for 40 minutes or more.
7) Powder of the complex of Java pepper extract was obtained, by spray drying under the condition of Inlet temp. 180~190° C., Outlet temp. 80~90° C.

In the following Example 2 to Example 7, the components and effect were confirmed using Java pepper extract comprising no dextrin. In other words, the concentrates of the Java pepper extract obtained by performing the steps 1) to 4) of Example 1 were freeze-dried and used (See left of FIG. 1, lab-scale).

Example 2. Analysis of Yield and Components of Java Pepper Extract

The extraction yield, flavonoid and piperine-based alkaloid content, and antioxidant activity through DPPH (2,2-Diphenyl-1-picrylhydrazyl) radical scavenging activity according to an extraction solvent used to extract Java pepper were measured (PREW: hot water extract of Java pepper, PREF: 50% (v/v) fermented spirit extract of Java pepper).

The extraction yield was measured based on the solid content of the Java pepper extract. The flavonoid and piperine-based alkaloid content was measured through HPLC-UVD (High Performance Liquid Chromatography-Ultraviolet detector) instrumental analysis, and measured by redissolving the hot water extract of Java pepper (PREW) and fermented spirit extract of Java pepper (PREF) in methanol at 10 mg(extract)/mL, respectively. The DPPH radical scavenging activity was measured by relative antioxidant activity of a 0.1% (w/v) Java pepper aqueous solution using ascorbic acid as a standard material. The measurement result was shown in Table 1 below.

TABLE 1

|  | Extraction yield | Piperine content (mg/g) | DPPH anti-oxidant activity |
|---|---|---|---|
| Java pepper hot water extract (PREW) | 3.8% | 1.93 ± 0.19 | 15% |
| Java pepper fermented spirit extract (PREF) | 5.44% | 135.02 ± 1.2 | 24% |

As could be confirmed in Table 1 above, the extraction yield was measured as 3.8% in the hot water extract of Java pepper, and it was measured as 5.44% in the fermented spirit extract of Java pepper.

Figure 2A:
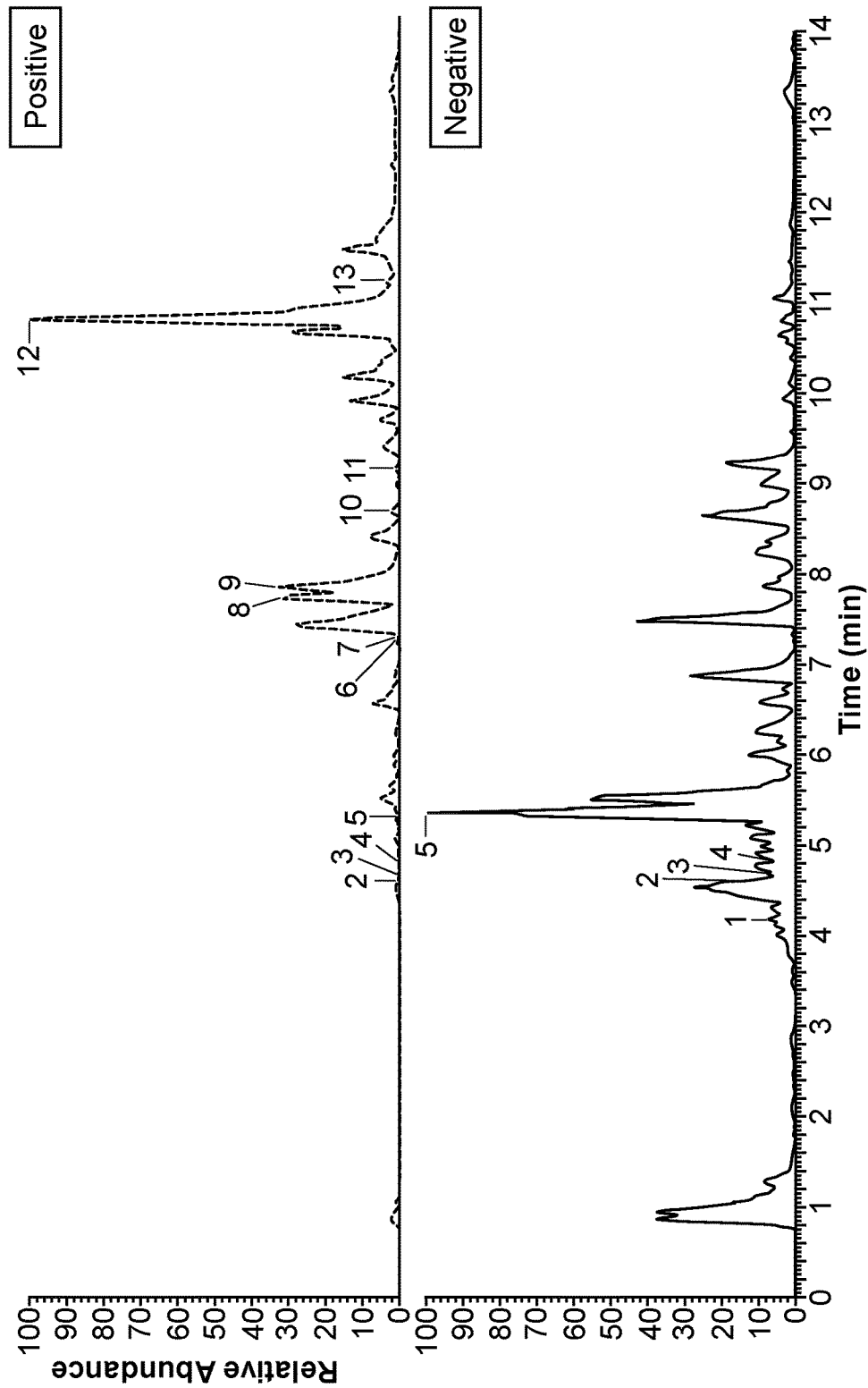

Qualitative analysis of flavonoid and piperine-based alkaloids of the hot water extract (PREW) and fermented spirit extract (PREF) of Java pepper was performed. For qualitative analysis, UHPLC-LTQ-Orbitrap-MS/MS instrument was used, and C18 UHPLC column with a diameter of 1.7 μm was used, and the analysis was conducted in an ionization mode. This result was shown in FIG. 2a and FIG. 2b. FIG. 2a is the result of qualitative analysis of the hot water extract (PREW) of Java pepper, and FIG. 2b is the result of qualitative analysis of the fermented spirit extract (PREF) of Java pepper. In FIG. 2a and FIG. 2b, the peak of RT (retention time) 7~10 minutes represents piperine-based alkaloid.

As could be confirmed in FIG. 2a, in the hot water extract (PREW) of Java pepper, 4 kinds of flavonoid components and 9 kinds of piperine-based alkaloid components were detected. In the fermented spirit extract (PREF) of Java pepper, 4 kinds of flavonoid components and 22 kinds of piperine-based alkaloid components were detected, and thereby, it was confirmed that various piperine-based alkaloid components were detected compared to the case in that Java pepper was extracted with hot water.

In addition, as could be confirmed in Table 1 above, the piperine content was measured as 1.93 mg/g in the hot water extract (PREW) of Java pepper, but the piperine content was measured as 135.02 mg/g in the fermented spirit extract (PREF) of Java pepper, and therefore, it was confirmed that the piperine content was higher compared to the case in that Java pepper was extracted with hot water.

Example 3. Measurement of In Vitro Vascular Endothelial Cell Viability

In the following Example 3 to Example 7, the freeze-dried matter of the concentrate of the hot water extract (PREW) and fermented spirit extract (PREF) of Java pepper extract obtained through the steps 1) to 4) of Example 1, was dissolved in the same solution as each extraction solvent to treat it to the cells. In other words, the freeze-dried matter of the concentrate of the hot water extract of Java pepper extract was dissolved in water (distilled water), and the freeze-dried matter of the fermented spirit extract of Java pepper extract was dissolved in 50% ethanol (fermented spirit) to treat it to the cells.

In order to show that the Java pepper extract is not harmful to vascular endothelial cells, a cell viability experiment was performed. WST-8 solution diluted with a medium was aliquoted into human dermal microvascular endothelial cells (HDMECs, purchased from PromoCell company, Sungwoo Life Science, Co., Ltd.), and they were stored in a 37° C., 5% $CO_2$ incubator for 1-4 hours. The WST-8 reagent is reduced by dehydrogenase in living cells to form formazan, and the produced amount of formazan is known as being in proportional to the cell viability. The WST-8 reagent is a reagent comprised in CCK-8 (Cell Counting Kit-8), and the CCK-8 was purchased from Dojindo Molecular Technologies, Inc.

After the hot water extract (PREW) and fermented spirit extract (PREF) of Java pepper extract obtained in Example 1 were treated into the HDMECs cells at various concentrations (12.5 μg/ml, 25 μg/ml, 50 μg/ml, 100 μg/ml, 200 μg/ml), respectively, the cell viability was measured using the CCK-8 reagent and the result was shown in FIG. 3.

As shown in FIG. 3, in the whole concentration range of the group in which the hot water extract (PREW) of Java pepper extract was treated, the cell viability increased. It was confirmed that the cell viability increased in a concentration-dependent manner in a concentration range of 0 to 100 μg/ml in the group in which the fermented spirit extract (PREF) of Java pepper extract.

Example 4. Measurement of Produced Amount of Nitrogen Monoxide

Nitrogen monoxide(NO, nitric oxide) is produced by nitric oxide synthase (endothelial nitric oxide synthase, eNOS) from an amino acid, arginine (L-arginine) in endothelial cells. nitrogen monoxide plays a key role of homeostasis maintenance of endothelial cells, and is diffused into vascular smooth muscle cells to induce vasorelaxation mediated by cyclic guanosine-5'-monophosphate (cGMP). In addition, nitrogen monoxide interrupts expression of inflammatory cytokines, attached molecules, and the like, and plays a key role of regulating vascular endothelial cell function. Therefore, the expression level of nitrogen monoxide in vascular endothelial cells when Java pepper extract was treated was measured.

A cell model in which L-NAME (Nw-Nitro-L-arginine methyl ester hydrochloride, CAS Number: 51298-62-5) was treated into HDMECs cells to inhibit production of nitrogen monoxide was prepared. L-NAME is known to play a role of interrupting that L-arginine is synthesized into nitrogen monoxide by nitric oxide synthase (eNOS, endothelial nitric oxide synthase) in vascular endothelial cells, and act to inhibit vasorelaxation. Therefore, for production of the cell model in which production of nitrogen monoxide is inhibited, L-NMAE was exposed into HDMECs cells at a concentration of 100 UM for 15 minutes.

Into the cell model, the Java pepper hot water extract and fermented spirit extract were treated, respectively, and the expression level of nitrogen monoxide was confirmed. A reagent, 4-amino-5-methylamino-2',7'-difluorofluorescein diacetate (DAF-FM DA, CAS Number: 254109-22-3) was diluted and treated into the HDMECs cells for 20~60 minutes, and the reagent was removed, and then the cells were washed with PBS. Then, the fluorescence was measured at a wavelength of ex 495 nm/em 515 nm, and this was shown in FIG. 4.

As shown in FIG. 4, it was confirmed that the produced amount of nitrogen monoxide was reduced, as the fluorescence was lower in the group in which L-NAME was treated (L-NAME(+)) compared to the group in which L-NAME was not treated (L-NAME(−)). As the result of treating the hot water extract (PREW) and fermented spirit extract (PREF) of Java pepper were treated into the group in which L-NAME was treated, respectively, (L-NAME(+)/PREW and L-NAME(+)/PREF)), it was confirmed that the produced amount of nitrogen monoxide which was reduced by L-NAME increased, and this increased to a level equal to or higher than that of the group in which L-NAME was not treated (L-NAME(−)).

Example 5. In Vitro Measurement of Expression Level of Vascular Endothelial Inflammatory Factor Protein A cell model in which vascular endothelial inflammation was induced by treating a lipopolysaccharide (LPS) substance into HDMECs cells was prepared. In cells exposed to an inflammation inducting substance, LPS, secretion of inflammatory cytokines is activated, and acute inflammation occurs. It has been known that when inflammation occurs in vascular endothelial cells, functions of normal endothelial cells are not carried out, and binding capacity between endothelial cells consisting of inner walls of blood vessels is weakened, and when inflammation becomes deepened, the function of anatomical barriers that prevent outflow of blood is lost. Therefore, in order to prepare a cell model in which vascular endothelial inflammation is induced, a vascular endothelial cell inflammation model was produced by exposing LPS into HDMECs at a concentration of 10 μg/mL. The vascular endothelial cell inflammation model produced as such was used in Examples 5 to 7 in the same manner.

The expression level of the inflammation factor was confirmed by treating the Java pepper hot water extract and fermented spirit extract into the cell model, respectively. After treating HDMECs cells with PBS twice, RIPA buffer was treated to make cell lysate. After centrifugation (13,500 rpm, 4° C., 20 minutes), the protein of supernatant was quantified, and an electrophoresis sample was prepared by adding loading buffer. After loading the same amount of protein by each group on acrylamide gel, electrophoresis was performed, and this was transferred to PVDF-membrane. After that, a band thickness by group was confirmed by blocking with 5% skim milk, attaching a primary antibody and a secondary antibody, and coloring with a fluorescence reagent. The band thickness and expression level of Nf-κB, ICAM-1 and VCAM-1 known as proteins which induce inflammation were confirmed, and GADPH was used as a housekeeping gene. This result was shown in FIG. 5.

As could be confirmed in FIG. 5, it was confirmed that the expression level of Nf-KB, ICAM-1 and VCAM-1 was increased in the group in which LPS was treated (LPS(+)) compared to the group in which LPS was not treated (LPS(−)). A positive control group was a group in which LPS was treated and rutin (CAS No. 153-18-4) was treated (Rut), and the rutin is a flavonoid-based component and is known as a component known to normally maintain vascular function. As the result of treating the hot water extract (PREW) and fermented spirit extract (PREF) of Java pepper into the group in which LPS was treated, respectively (LPS(+)/PREW and LPS(+)/PREF), it was confirmed that the expression level of the inflammation factor protein increased by LPS was reduced.

Example 6. In Vitro Measurement of Vascular Endothelial Binding Capacity Reinforcement Factor Protein A cell model in which vascular binding capacity was weakened by treating a lipopolysaccharide (LPS) substance into HDMECs cells was prepared. The cell model was prepared by the same method as the cell model prepared in Example 5.

The expression level of Tie2 protein was confirmed by treating the Java pepper hot water extract and fermented spirit extract into the cell model, respectively. Tie2 protein is a receptor present in vascular endothelial cells and is known to promote stabilization of blood vessels, and is known to increase and stabilize binding capacity between vascular wall cells and endothelial cells by forming binding with angiopoietin-1 secreted from pericytes. The expression level of Tie2 protein was measured by the same method as the method used in Example 5.

The result of treating the Java pepper hot water extract and fermented spirit extract into the HDMECs cells, respectively, and measuring the expression level of Tie2 protein was shown in FIG. 6.

As shown in FIG. 6, the expression level of Tie2 protein in the group in which LPS was treated (LPS(+)) was reduced compared to the group in which LPS was not treated (LPS(−)). A positive control group is a group in which LPS is treated and rutin is treated (Rut).

As the result of treating the hot water extract (PREW) and fermented spirit extract (PREF) of Java pepper into the group in which LPS was treated, respectively (LPS(+)/PREW and LPS(+)/PREF), the expression level of Tie2 protein reduced by LPS increased. In addition, as the result of treating the hot water extract (PREW) and fermented spirit extract (PREF) of Java pepper into the group in which LPS was not treated, respectively (LPS(−)/PREW and LPS (−)/PREF), it was confirmed that the expression level of Tie2 protein increased significantly.

Example 7. In Vitro Measurement of Vascular Permeability

Vascular endothelium is a cell layer covering the vascular lumen, where substances such as oxygen, nutrients, wastes, and the like, and exhibits a selective barrier function for material exchange between intravascular space and surrounding tissue. Numerous cytokines (TNF-α, IL-1, etc.) involved in this permeability are present, and vascular permeability increases with secretion of inflammation mediators. When vascular permeability is damaged, systemic diseases such as cancer, diabetes, stroke, hypertension and the like occur. When capillary permeability increases, proteins in blood move into tissue, and more moisture moves into tissue due to osmotic pressure, thereby causing oedema.

A cell model in which vascular permeability acceleration was induced by treating a lipopolysaccharide (LPS) substance into HDMECs cells was prepared. The cell model was prepared by the same method as the cell model prepared in Example 5.

The vascular permeability was confirmed by treating the Java pepper hot water extract (PREW) and fermented spirit extract (PREF) into the cell model, respectively.

The HDMECs cells were cultured in a chamber of a Collagen-I-coated transwell to form a monolayer. In 5 minutes after FITC-dextran diluted in a medium in the Chamber was aliquoted, the amount of FITC-dextran permeated into a bottom plate was measured by fluorescence at ex485 nm/em520 nm, and the permeability (vascular permeability) was calculated, and this was shown in FIG. 7.

As shown in FIG. 7, the vascular permeability increased in the group in which LPS was treated (LPS(+)) compared to the group in which LPS was not treated (LPS(−)). As the result of treating the hot water extract (PREW) and fermented spirit extract (PREF) of Java pepper into the group in which LPS was treated, respectively (LPS(+)/PREW and LPS(+)/PREF), it was confirmed that the vascular permeability increased by LPS was reduced.

Example 8. Comparison Result Experiment with Long Pepper

By the substantially same method as the method described in step 1) to step 4) of Example 1, Java pepper extract obtained by extracting Java pepper with a 50% (v/v) aqueous ethanol solution was prepared.

As a comparison group, by extracting long pepper (using fruit parts of long pepper, acquired from CK Co., Ltd.) by the substantially same method as the above method, long pepper extract obtained by extracting long pepper with a 50% (v/v) aqueous ethanol solution was prepared.

By the substantially same method as the method described in Example 5, a cell model, in which vascular endothelial inflammation and vascular binding capacity were weakened by treating LPS into human dermal microvascular endothelial cells (HDMECs), was prepared.

The expression level of inflammation factor proteins (ICAM-1 and VCAM-1) was measured by the substantially same method as the method described in Example 5 by treating the Java pepper extract and long pepper extract into the cell model, respectively, and the result was shown in FIG. 8 and FIG. 9 below.

As could be confirmed in FIG. 8 and FIG. 9 above, compared to the control group in which nothing was treated into the HDMECs cells (Control), in case of the group in which LPS was treated (LPS), the expression level of ICAM-1 and VCAM-1 proteins increased. In case of the experimental group in which LPS was treated and Java pepper extract was treated into the HDMECs cells (L+PR), it was confirmed that the expression level of ICAM-1 and VCAM-1 proteins increased by LPS treatment was significantly reduced.

On the other hand, in case of the experimental group in which LPS was treated and long pepper extract was treated into the HDMECs cells (L+PL), compared to the experimental group in which only LPS was treated into the HDMECs cells (LPS), it was confirmed that the expression level of ICAM-1 and VCAM-1 proteins rather further increased, thereby exhibiting an absolutely opposite effect to the experimental group in which Java pepper extract was treated.

As could be confirmed from the experimental result, it was confirmed that the long pepper extract belonging to congeneric to Java pepper rather increased the expression level of the inflammation factor proteins, but the Java pepper extract, which is the present invention, reduced the expression level of the inflammation factor proteins.

Example 9. Experimental Data According to Concentration of Extraction Solvent of Java Pepper By the substantially same method as the method described in the step 1) to step 4) of Example 1, Java pepper extract obtained by extracting Java pepper with a 50% (v/v) aqueous ethanol solution was prepared. As a comparison group, Java pepper extract obtained by extracting Java pepper with water (0% aqueous ethanol solution) or aqueous ethanol solution at various concentrations (30%, 50%, 70%, 90%) was prepared.

1) Measurement of Nitrogen Monoxide Production Inhibitory Activity

Nitrogen monoxide (nitric oxide, NO) refers to a very important signal molecule which performs various regulations of physiological process molecules from many tissues. Nitrogen monoxide possesses blood coagulation and blood pressure regulation function and immune function against cancer cells, but when it is present in excess, it has a harmful effect on the human body, causing not only cell damage but also inflammation reactions. Raw264.7 cells of $2.5 \times 10^5$ cells/well were aliquoted into a 96 well plate, and then cultured at 5% $CO_2$ 37° C. and used. By treating the Java pepper extracted prepared above after treating LPS 1 mg/me into the aliquoted cells, they were cultured for 24 hours. After that, nitrogen monoxide secreted from the medium was treated with Griss reaction for 15 minutes, and then the optical density was measured at 540 nm, and the expression level of nitrogen monoxide was confirmed and the result was shown in FIG. 10.

In FIG. 10, in the control group in which LPS was treated and the Java pepper extract was not treated into the RAW264.7 cells (Con(Rut)), a large amount of nitrogen monoxide was produced. As the result of confirming the nitrogen monoxide production inhibitory effect of Java pepper extract by ethanol extraction concentration in the RAW264.7 cells stimulated by LPS, the nitrogen monoxide production inhibitory effect could be confirmed at all the concentrations. Among them, in case that the Java pepper extract obtained by extracting Java pepper with a 50% (v/v) aqueous ethanol solution was treated, compared to the case in that the Java pepper extract obtained by extracting Java pepper with water or an aqueous ethanol solutions at other concentrations was treated, it was confirmed that the nitrogen monoxide production inhibitory activity was the highest.

2) Measurement of Expression Level of Ang-1 Protein

By the substantially same method as the method described in Example 6, a cell model in which vascular endothelial inflammation was induced by treating a lipopolysaccharide (LPS) substance into human dermal microvascular endothelial cells (HDMECs) was prepared, and then the Java pepper extract prepared above was treated, and the expression level of Ang-1 protein was measured, and the result was shown in FIG. 11.

As could be confirmed in FIG. 11 above, compared to the control group in which nothing was treated into the HDMECs cells (Con), in case of the group in which LPS was treated into the HDMECs cells (LPS), the expression level of Ang-1 protein was reduced. As the result of treating LPS and treating the Java pepper extract into the HDMECs cells, it was confirmed that in case of treating the Java pepper extract obtained by extracting Java pepper with a 50% (v/v) aqueous ethanol solution, compared to the case in that the Java pepper extract obtained by extracting Java pepper with water or aqueous ethanol solutions at other concentrations, the expression level of Ang-1 protein increased significantly.

From the above description, those skilled in the art to which the present invention pertains will be able to understand that the present invention may be embodied in other specific forms without changing its technical spirit or essential characteristics. In this regard, the examples described above should be understood in all respects as illustrative and not restrictive. The scope of the present invention should be construed as including all changed or modified forms derived from the meaning and scope of the following claims and their equivalents rather than the above description in the scope of the present invention.

The invention claimed is:

1. A method for treatment of a disease related to vascular dysfunction, comprising administering an effective amount of *Piper retrofractum* extract into a subject in need of treatment of the disease related to vascular dysfunction,
   wherein the disease related to vascular dysfunction is selected from the group consisting of varicose vein, edema, venous insufficiency, deep vein thrombosis, venous hyperlipidemia, venous thrombosis, venous cerebrovascular disease, venous renovascular disease, gangrene, Buerger's disease, Raynaud disease, hand-foot syndrome, hereditary telangiectasia, capillary leak syndrome and arrhythmia.

2. The method according to claim 1, wherein the *Piper retrofractum* extract is obtained by extracting *Piper retrofractum* with at least one extraction solvent selected from the group consisting of water and straight chain or branched alcohols having 1 to 4 carbon atoms.

3. The method according to claim 1, wherein the *Piper retrofractum* extract is obtained by extracting *Piper retrofractum* with hot water.

4. The method according to claim 1, wherein the *Piper retrofractum* extract is obtained by extracting *Piper retrofractum* with an aqueous ethanol solution.

5. The method according to claim 1, wherein the *Piper retrofractum* extract is obtained by extracting *Piper retrofractum* with a 40 to 60% aqueous ethanol solution.

6. The method according to claim 1, wherein the *Piper retrofractum* extract further comprises dextrin.

7. The method according to claim 1, wherein the *Piper retrofractum* extract comprises piperine at a content of 1 to 1000 mg/g.

* * * * *